United States Patent
Kontos et al.

(10) Patent No.: US 8,634,610 B2
(45) Date of Patent: Jan. 21, 2014

(54) SYSTEM AND METHOD FOR ASSESSING CANCER RISK

(75) Inventors: Despina Kontos, Philadelphia, PA (US); Predrag Bakic, Philadelphia, PA (US); Andrew D. A. Maidment, Villanova, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 754 days.

(21) Appl. No.: 12/488,871

(22) Filed: Jun. 22, 2009

(65) Prior Publication Data

US 2009/0324049 A1 Dec. 31, 2009

Related U.S. Application Data

(60) Provisional application No. 61/074,321, filed on Jun. 20, 2008.

(51) Int. Cl.
*G06K 9/00* (2006.01)
*G06K 9/46* (2006.01)
*G06K 9/66* (2006.01)

(52) U.S. Cl.
USPC .......................... 382/128; 382/115; 382/190

(58) Field of Classification Search
None
See application file for complete search history.

(56) References Cited

U.S. PATENT DOCUMENTS

| | | | |
|---|---|---|---|
| 5,796,862 A * | 8/1998 | Pawlicki et al. | 382/132 |
| 6,282,305 B1 * | 8/2001 | Huo et al. | 382/128 |
| 7,218,766 B2 | 5/2007 | Eberhard et al. | |
| 7,298,876 B1 | 11/2007 | Marshall et al. | |
| 7,751,528 B2 * | 7/2010 | Zhou et al. | 378/37 |
| 2004/0258310 A1 | 12/2004 | Giger et al. | |
| 2006/0228015 A1 * | 10/2006 | Brockway et al. | 382/132 |
| 2007/0258626 A1 * | 11/2007 | Reiner | 382/115 |
| 2007/0280525 A1 * | 12/2007 | Basilico et al. | 382/132 |
| 2008/0144940 A1 * | 6/2008 | Russakoff | 382/203 |
| 2008/0226137 A1 * | 9/2008 | Benaron et al. | 382/115 |
| 2009/0141859 A1 | 6/2009 | Gkanatsios et al. | |
| 2010/0098306 A1 * | 4/2010 | Madabhushi et al. | 382/128 |

OTHER PUBLICATIONS

Li, "Computerized analysis of mammographic parenchymal patterns for assessing breast cancer risk: Effect of ROI size and location", 2004, Med. Phys. 31 (3), pp. 549-555.*
Kontos, "Fast and effective characterization for classification and similarity searches of 2D and 3D spatial region data", 2005, Pattern Recognition Society v. 38, pp. 1831-1846.*
Breitenstein, "Comparison of Three Tissue Composition Measurement Techniques Using Digital Mammograms—A Signal-to-Noise Study", 1998, Journal of Digital Imaging, vol. 11, No. 3, pp. 137-150.*

(Continued)

*Primary Examiner* — Bhavesh Mehta
*Assistant Examiner* — David F Dunphy
(74) *Attorney, Agent, or Firm* — RatnerPrestia

(57) ABSTRACT

Methods and systems for determining a probabilistic assessment of a person developing cancer are disclosed. The probabilistic assessment may include receiving a digital breast image of a person, selecting a region of interest within the received breast image, and analyzing this selected region of interest with respect to texture analysis. A probabilistic assessment may then be determined through the use of a logistic regression model based on the texture analysis within the region of interest and personal risk factors. A probabilistic assessment may also be determined through the use of a linear regression model based on the texture analysis within the region of interest and a known cancer indicator or risk factor.

23 Claims, 14 Drawing Sheets

(56) References Cited

OTHER PUBLICATIONS

Kontos et al, "Analysis of Parenchymal Texture Properties in Breast Tomosynthesis Images," 2007, In Proc. SPIE Medical Imaging Computer Aided Diagnosis, vol. 6514, pp. 1-22.*
Mitchell D. Schnall: Breast Cancer Screening Enters Era of Personalized Care, RSNA News, Mar. 2008.
Kontos, D., Bakic, P.R. and Maidment, A.D.A.: Texture in Digital Breast Tomosynthesis: A Comparison between Mammographic and Tomographic Characterization of Parenchymal Properties. In: Giger, M.L. and Karssemeijer, N. (eds.): *In Proc. SPIE Medical Imaging: Computer Aided Diagnosis*, vol. 6915, San Diego, CA, 2008.
Huo Z. and Giger M.L., W.D.E., Zhong W., Cummings S., Olopade O.I.: Computerized analysis of mammographic parenchymal patterns for breast cancer risk assessment: feature selection. Medical Physics, 27(1):4-12, 2000.
Li, H., Giger, M.L., Huo, Z., Olopade, O.I., Lan, L., Weber, B.L. and Bonta, I.: Computerized analysis of mammographic parenchymal patterns for assessing breast cancer risk: effect of ROI size and location. Medical Physics, 31(3):549-555, 2004.
Huo, Z., Giger, M.L., Olopade, O.I., Wolverton, D.E., Weber, B.L., Metz, C.E., Zhong, W. and Cummings, S.A.: Computerized analysis of digitized mammograms of BRCA1 and BRCA2 gene mutation carriers. Radiology, 225(2):519-526, 2002.
Li, H., Giger, M.L., Olopade, O.I. and Lan, L.: Fractal analysis of mammographic parenchymal patterns in breast cancer risk assessment. Academic Radiology, 14(5):513,521, 2007.
Kontos, D. and Megalooikonomou, V.,: Fast and effective characterization for classification and similarity searches of 2D and 3D spatial region data,. Pattern Recognition 38:1831-1846, 2005.
Li, H., Giger, M.L., Olopade, O.I., and Chinander, M.R.,: Power spectral analysis of mammographic parenchymal patterns for breast cancer risk assessment. Journal of Digital Imaging, 2007.
Kontos, D., Bakic, P.R., Maidment, A.D.A.: Analysis of Parenchymal Texture Properties in Breast Tomosynthesis Images. In: Giger, M.L., and Karssemeijer, N. (eds.): *In Proc. SPIE Medical Imaging Computer Aided Diagnosis*. vol. 6514, San Diego, CA, 2007.
Kontos, D., Bakic, P.R., Maidment, A.D.A.: Towards developing quantitative imaging methods for Breast Cancer Risk assessment. $6^{th}$ Annual Biomedical Postdoc Research Symposium, Univ. of Pennsylvania: Oct. 24, 2007.
Kontos, D., Bakic, P.R., Maidment, A.D.A.: Presentation on Parenchymal Texture Analysis in Digital Breast Tomosynthesis Towards Developing Biomarkers for Breast Cancer Risk. $32^{nd}$ Annual Eugene P. Pendergrass Symposium, Jun. 2007.
Kontos, D., Bakic, P., Maidment, A.: Towards Developing Tomosynthesis Texture Biomarkers for Breast Cancer Risk. *X-Cite* Lab, Physics Section, Dept. of Radiology, Univ. of Pennsylvania: Oct. 22, 2007.
Kontos, D., Zhang, C., Ruiter, N.V., Bakic, P.R., and Maidment, A.D.A., "Evaluating the Effect of Tomosynthesis Acquisition Parameters on Image Texture: A Study Based on an Anthropomorphic Breast Tissue Software Model," in: E. Krupinski (ed.), International Workshop on Digital Mammography (IWDM), Springer Lectures Notes in Computer Science, Tucson, AZ, 2008.
Kontos, D., Bakic, P.R., Troxel, A.B., Conant, E.F., and Maidment, A.D.A., "Digital Breast Tomosynthesis Parenchymal Texture Analysis for Breast Cancer Risk Estimation: A Preliminary Study," In: E. Krupinski (ed.), International workshop on Digital Mammography (IWDM), Springer Lectures Notes in Computer Science, Tucson, AZ, 2008.
Kontos, D., Bakic, P.R., and Maidment, A.D.A., "Breast Tissue Classification in Digital Breast Tomosynthesis Images using Texture Features," The American Association of Physicists in Medicine (AAPM) $50^{th}$ Annual Meeting, Houston, TX, 2008.
Kontos, D., Bakic, P.R., and Maidment, A.D.A., "Towards Developing Quantitative Imaging Methods for Breast Cancer Risk Assessment: A Comparison between Mammographic and Tomographic Characterization of Parenchymal Texture," University of Pennsylvania $6^{th}$ Annual Biomedical Postdoc Research Symposium, Oct. 24, 2007.
Kontos, D., Bakic, P.R., and Maidment, A.D.A., "Parenchymal Texture Analysis in Digital Breast Tomosynthesis: Towards Developing Biomarkers for Breast Cancer Risk," $32^{nd}$ Annual Eugene P. Pendergrass Symposium, Department of Radiology, University of Pennsylvania, Jun. 22, 2007.
Kontos, D., Bakic, P.R., and Maidment, A.D.A., "Analysis of Parenchymal Texture Properties in Breast Tomosynthesis Images," University of Pennsylvania $5^{th}$ Annuel Biomedical Postdoc Research Symposium, Oct. 11, 2006.
Kontos, D., Bakic, P.R., Troxel, A.B., Conant, E.F., and Maidment, A.D.A., "Parenchymal Texture Analysis in Digital Breast Tomosynthesis for Computer-Assisted Risk Estimation (CARe) of Breast Cancer: A Preliminary Evaluation," Radiological Society of North America (RSNA) Annual Meeting, Chicago, IL, 2008.
Kontos, D., Bakic, P.R., Troxel, A.B., Conant, E.F., and Maidment, A.D.A., "Parenchymal Pattern Analysis in Digital Breast Tomosynthesis: Towards Developing Imaging Biomarkers of Breast Cancer Risk." Academic Radiology, 2008.
Kontos, D., "Tomosynthesis Texture Biomarkers for Computer-Assisted Risk Estimation (Care) of Breast Cancer," Postdoctoral Fellowship, Komen Foundation, Start Date: On or after Jul. 1, 2008.
Kontos, D., Research Fellow Grant by RSNA Research & Education Foundation for tomosynthesis imaging biomarkers for breast cancer risk, Start Date: On or after Jul. 1, 2006.
Kontos, D., Research Fellow Grant by RSNA Research & Education Foundation for "Computer-Assisted Risk Estimation (CARe) from Breast Tomosynthesis Images," Start Date: On or after Jul. 1, 2007.

* cited by examiner (570)

Stepwise Multiple Linear Regression of Combined Texture Features vs. SNR

Model Summary:

| R | R Square | Adjusted R Square | Std. Error of the Estimate |
|---|---|---|---|
| 0.96 | 0.921 | 0.92 | 0.013 |

Coefficients:

| | B | Std. Error | t | Sig. |
|---|---|---|---|---|
| (Constant) | 4.101 | 0.008 | 523.623 | 0.000 |
| Contrast | 0.291 | 0.033 | 8.742 | 0.000 |
| Energy | -0.302 | 0.014 | -21.217 | 0.000 |
| Fractal Dimension | 0.374 | 0.038 | 9.953 | 0.000 |

Fig. 9

Stepwise Multiple Linear Regression of Combined Texture Features and Acquisition Parameters vs. SNR

Model Summary:

| R | R Square | Adjusted R Square | Std. Error of the Estimate |
|---|---|---|---|
| 0.974 | 0.949 | 0.946 | 0.009 |

Coefficients:

| | B | Std. Error | t | Sig. |
|---|---|---|---|---|
| (Constant) | 4.101 | 0.006 | 639.891 | 0.000 |
| Skewness | -0.185 | 0.034 | -5.442 | 0.000 |
| Coarseness | -0.483 | 0.082 | -5.871 | 0.000 |
| Contrast | 0.389 | 0.059 | 6.597 | 0.000 |
| Energy | -1.250 | 0.150 | -8.310 | 0.000 |
| Homogeneity | 0.319 | 0.067 | 4.747 | 0.000 |
| Fractal Dimension | 0.443 | 0.039 | 11.317 | 0.000 |
| kV | 0.098 | 0.010 | 9.474 | 0.000 |
| Target | 0.039 | 0.008 | 4.949 | 0.000 |
| Filter | 0.029 | 0.009 | 3.294 | 0.001 |

Fig. 10

Combined texture features vs. dose

| Model Summary | | | |
|---|---|---|---|
| R | $R^2$ | Adjusted $R^2$ | Std. Error |
| 0.959 | 0.919 | 0.917 | 0.099 |

| Coefficients | | | | |
|---|---|---|---|---|
| | B | Std. Error | t | Sig. |
| (intercept) | 4.207 | 0.021 | 198.549 | 0.000 |
| Skewness | -0.708 | 0.083 | -8.485 | 0.000 |
| Coarseness | -0.640 | 0.165 | -3.889 | 0.000 |
| Contrast | 0.582 | 0.096 | 6.074 | 0.000 |
| Energy | -2.162 | 0.165 | -13.131 | 0.000 |
| FD | 0.704 | 0.105 | 6.732 | 0.000 |

FIG. 11

Combined texture features, target, filter, kV vs. dose

| Model Summary | | | |
|---|---|---|---|
| R | $R^2$ | Adjusted $R^2$ | Std. Error |
| 0.963 | 0.928 | 0.926 | 0.088 |

| Coefficients | | | | |
|---|---|---|---|---|
| | B | Std. Error | t | Sig. |
| (intercept) | 4.207 | 0.020 | 209.818 | 0.000 |
| Skewness | -0.683 | 0.096 | -7.141 | 0.000 |
| Coarseness | -1.462 | 0.230 | -6.347 | 0.000 |
| Contrast | 1.201 | 0.183 | 6.554 | 0.000 |
| Energy | -3.904 | 0.404 | -9.655 | 0.000 |
| Homogeneity | 0.825 | 0.194 | 4.262 | 0.000 |
| FD | 1.018 | 0.121 | 8.423 | 0.000 |
| kV | 0.152 | 0.030 | 5.015 | 0.000 |

FIG. 12

Beta $b$ Coefficients, $R^2$ Values, and $P$ Values for the Fitted Regression Models of Each DM and DBT Texture Descriptor

| Variable | DM | | | 3D DBT | | |
|---|---|---|---|---|---|---|
| | $b$ | $R^2$ | $P$ | $b$ | $R^2$ | $P$ |
| Skewness | −0.08 | 0.01 | .50 | 0.06 | 0.03 | .33 |
| Coarseness | −0.2 × 10⁻⁴ | 0.01 | .55 | 0.7×10⁻⁵ | 0.17 | .008 |
| Contrast | −0.91 | 0.05 | .15 | −588 | 0.10 | .05 |
| Energy | −0.006 | 0.06 | .14 | −0.005 | 0.07 | .09 |
| Homogeneity | 0.005 | 0.10 | .04 | 0.009 | 0.08 | .09 |
| Fractal dimension | 0.04 | 0.18 | .006 | 0.04 | 0.16 | .01 |
| PCA | 0.19 | 0.01 | .46 | 0.84 | 0.21 | .003 |

Fig. 13

SYSTEM AND METHOD FOR ASSESSING CANCER RISK

RELATED APPLICATIONS

This application claims priority to U.S. Provisional Patent Application Ser. No. 61/074,321, filed Jun. 20, 2008, titled System and Method for Assessing Cancer Risk, which is incorporated fully herein by reference.

FIELD OF THE INVENTION

The present invention relates to assessing a person's risk for developing cancer. Specifically, texture features of a person's image along with risk factors of the person are utilized to determine a probabilistic assessment for developing cancer.

BACKGROUND OF THE INVENTION

Screening digital mammography (DM) and digital breast tomosynthesis (DBT) are tools for identifying latent breast cancers within a population, leading to improved outcomes of reduced mortality. For women at increased risk of breast cancer, however, magnetic resonance imaging (MRI) although more expensive than DM and DBT, may provide superior capabilities in identifying early stage cancers, thereby justifying their increased cost. As a result, cost reimbursement has been authorized for using MRI to screen women within high risk categories. There is an ever present desire to reduce medical cost by utilizing less expensive medical procedures, while maintaining a high quality of care. The present invention addresses this need among others.

SUMMARY OF THE INVENTION

In accordance with one aspect of the invention, methods and systems are disclosed for assessing the risk of developing cancer. The risk of developing cancer may be assessed by receiving an image of a person, analyzing the image to obtain values representing characteristics of the image, obtaining risk factors associated with the person, determining a probabilistic assessment of the person developing cancer based on the obtained values and the obtained risk factors, and storing the probabilistic assessment.

In accordance with another aspect of the invention, methods are disclosed for selecting a region of interest (ROI) within a breast image. The ROI may be selected by receiving a breast image, comparing the breast image with other breast images to establish anatomic correspondences, and mapping a region identifier onto the breast image to select the ROI based on the anatomic correspondences.

BRIEF DESCRIPTION OF THE DRAWINGS

The invention is best understood from the following detailed description in connection with the accompanying drawings, with like elements having the same reference numerals. According to common practice, the various features of the drawings are not drawn to scale. On the contrary, the dimensions of the various features are arbitrarily expanded or reduced for clarity. The letter N may be used to refer to a non-specific number of elements. Included in the drawings are the following figures:

FIG. 9 is a table of the linear regression of texture features versus SNR in accordance with an aspect of the present invention;

FIG. 10 is a table of the linear regression of texture features and acquisition parameters versus SNR in accordance with an aspect of the present invention;

FIG. 11 is a table of the linear regression of texture features versus dose in accordance with an aspect of the present invention;

FIG. 12 is a table of the linear regression of texture features and acquisition parameters versus dose in accordance with an aspect of the present invention; and FIG. 13 is a table of the linear regression of texture features versus breast density in accordance with an aspect of the present invention.

DETAILED DESCRIPTION OF THE INVENTION

Breast cancer risk may be assessed based solely on Gail risk factors, which are described below. A limitation of this type of assessment model is its reliance of population statistics to identify at-risk persons. As a result, it does not accurately predict a person's specific lifetime risk of developing cancer. Other techniques focus on utilizing tissue characteristics within an image such as mammographic breast density assessment to identify person-specific markers of breast cancer risk either as a substitute or as an adjunct to the Gail risk tool. Nevertheless, these techniques are not certain, mostly do to the subjective nature of the density assessment. Additionally, studies suggest a relationship between mammographic parenchymal tissue and the risk of developing breast cancer.

Parenchymal texture patterns in X-ray breast images are formed by the fatty, glandular, and stromal breast tissues.

Figure 1:
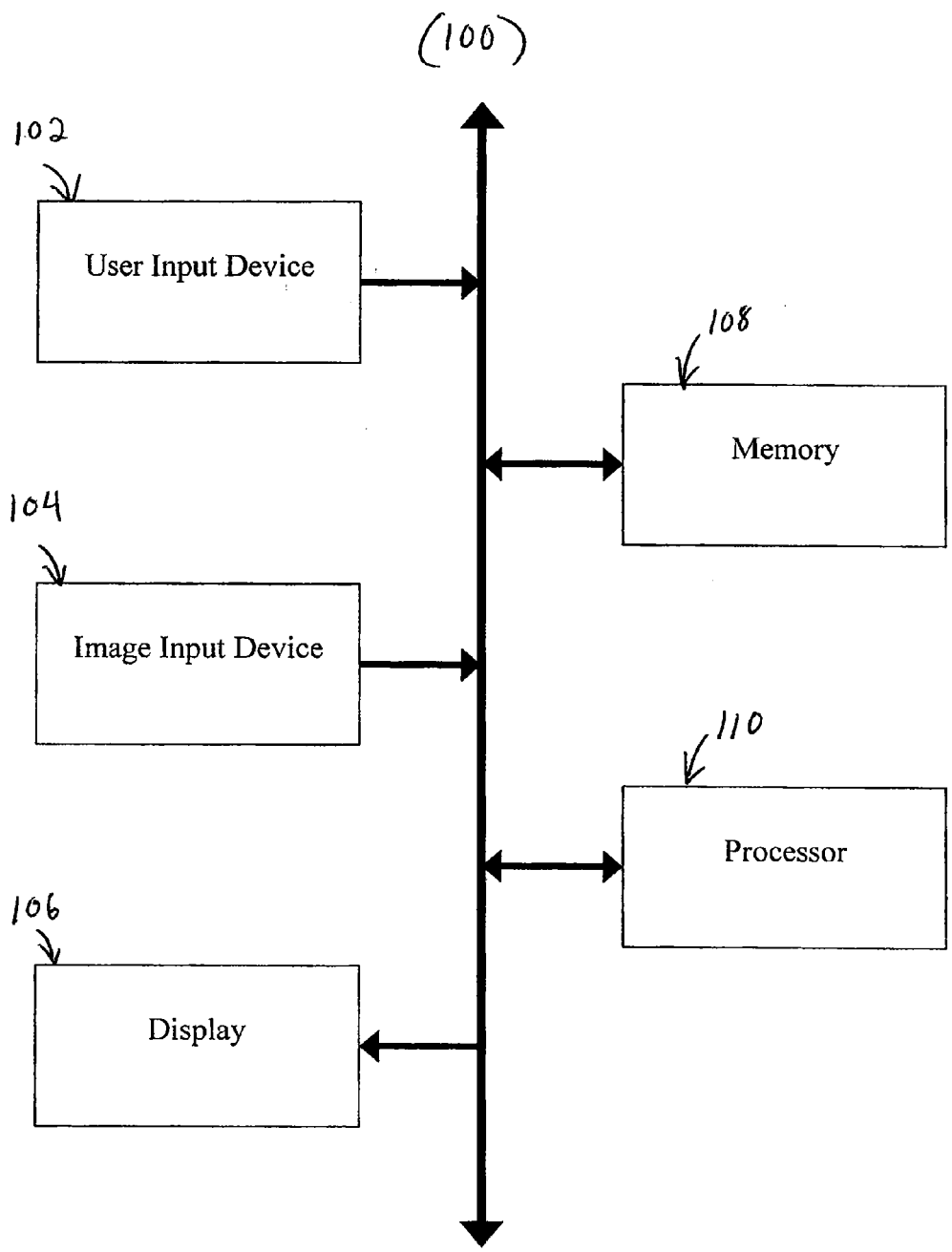
FIG. 1 is a block diagram illustrating a computer architecture for assessing breast risk in accordance with an aspect of the present invention.

FIG. 1 is a block diagram illustrating one embodiment of a computer system 100 for assessing the risk of a person developing cancer. The computer system 100 includes a user input device 102, an image input device 104, a display device 106, a memory 108 and a processor 110. In one example, user input device 102 may be a computer mouse and keyboard that enables information to be manually input into system 100. In one example, image input device 104 may be an X-ray device that provides X-ray images such as DM and/or DBT images to system 100. Images may also include other digital images such as MRI, ultrasound, CT, optical, etc. In another example, image input device 104 may be another computer or a memory device for providing images to system 100. In one example, display 106 may be a computer monitor that visually displays information. Suitable user input devices, image input devices (including medical acquisition systems and picture archiving and communication systems (PACs)), displays, memories, and processors for use in accordance with the present invention will be understood by one of skill in the art from the description herein.

In an embodiment of the present invention, and as will be described in further detail below, the illustrated computer system 100 operates in the following manner: X-ray images of breast tissue are input through image input device 104. Person information and other parameters associated with the assessment of cancer risk are input through user input device 102. The output of user input device 102 and image input device 104 are stored in memory 108 and processed by processor 110. Processor 110 processes the input information and the image information, assesses the risk of cancer, stores the results in memory 108, and displays the cancer risk assessment results on display 106.

Figure 2:
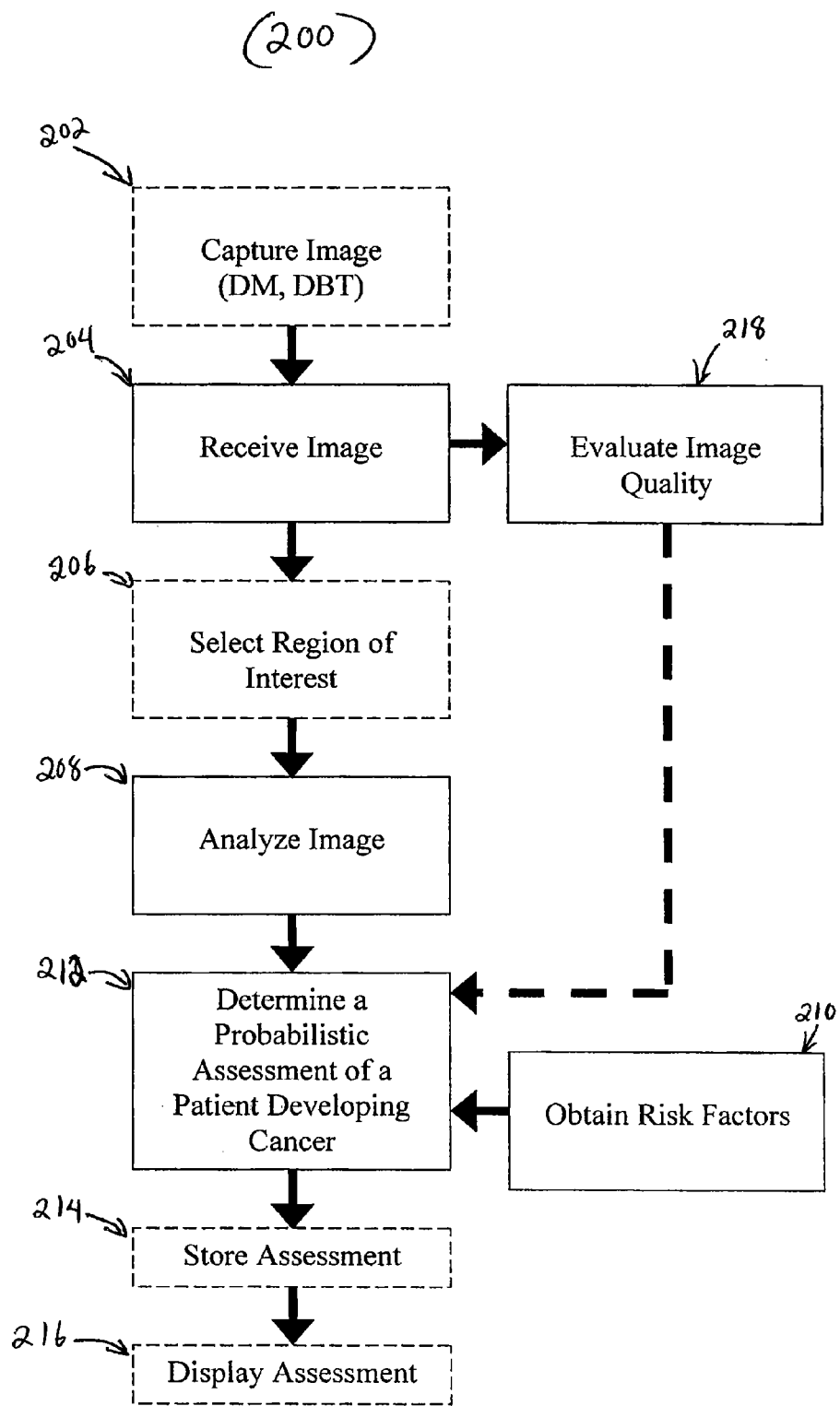
FIG. 2 is a flow diagram illustrating steps for assessing cancer risk in accordance with an aspect of the present invention.

FIG. 2 depicts a flow diagram 200 of exemplary steps for assessing breast cancer risk in accordance with an aspect of the present invention. Briefly, in step 202 an image is captured, in step 204 the image is received, in optional step 218 the image quality is evaluated, in optional step 206 a ROI within the received image is selected, in step 208 the image is analyzed, in step 210 risk factors of a person are determined, step 212 the probabilistic assessment of the person developing cancer is calculated based on the analysis of the image and the determined risk factors, in step 214 the assessment is stored in memory, and in step 216 the assessment of the person developing cancer is displayed.

Figure 3A:
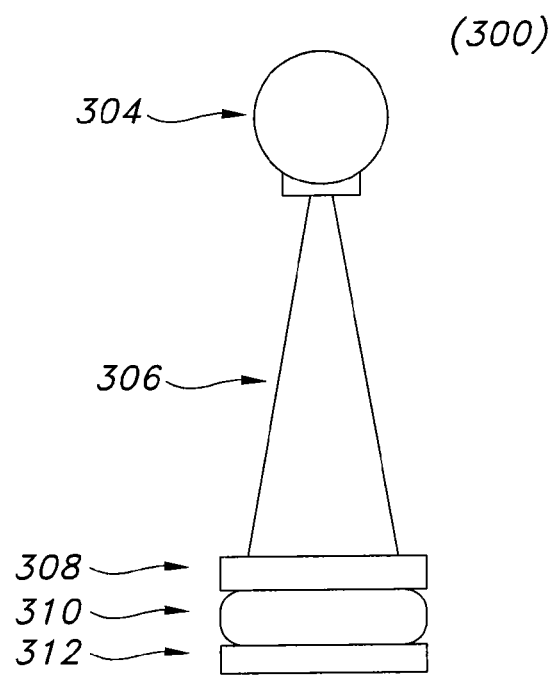
FIG. 3a is an image depicting a prior art digital mammography (DM) system.
Figure 3B:
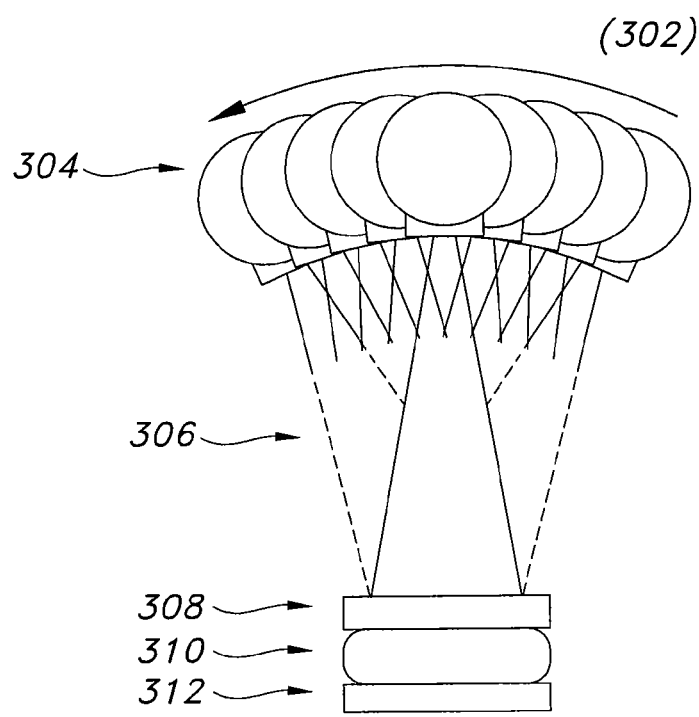
FIG. 3b is an image depicting a prior art digital breast tomosynthesis (DBT) system.
Figure 5A:
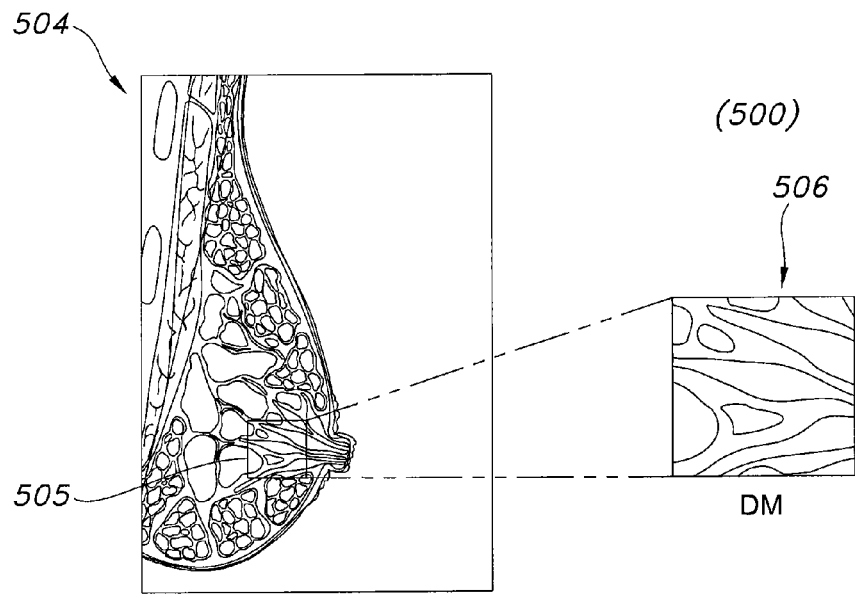
FIG. 5a is an image illustrating the selection of a ROI within a DM image in accordance with an aspect of the present invention.

The steps of flow diagram 200 will now be described in detail. In step 202, an image is captured, e.g., by or via image input device 104. In an exemplary embodiment, a breast image is captured. In one embodiment, an image of a breast is captured using, for example, DM (FIG. 3a) or DBT (FIG. 3b). Other types of images may include digital imaging modalities such as MRI, ultrasound, CT, optical imaging, etc. In the DM imaging system 300 depicted in FIG. 3a, two-dimensional (2D) images are produced by a compressed projection of the three-dimensional (3D) breast volume. As shown in FIG. 3a, breast 310 is inserted between compression plate 308 and detector 312. X-rays 306 are then transmitted in the direction of the breast 310 via X-ray tube 304. As X-rays 306 pass through breast 310, they are detected by detector 312 to produce a breast image 504 as shown in FIG. 5a. A consideration in the use of DM is that the images produced reflect the properties of the parenchymal breast tissue and the properties of other tissue (e.g., skin and subcutaneous fat layers), which may make it more difficult to assess breast cancer. In general, skin and subcutaneous fat could be considered noise in terms of image-based risk breast cancer characterization, thus increasing the likelihood of erroneous results.

Figure 5B:
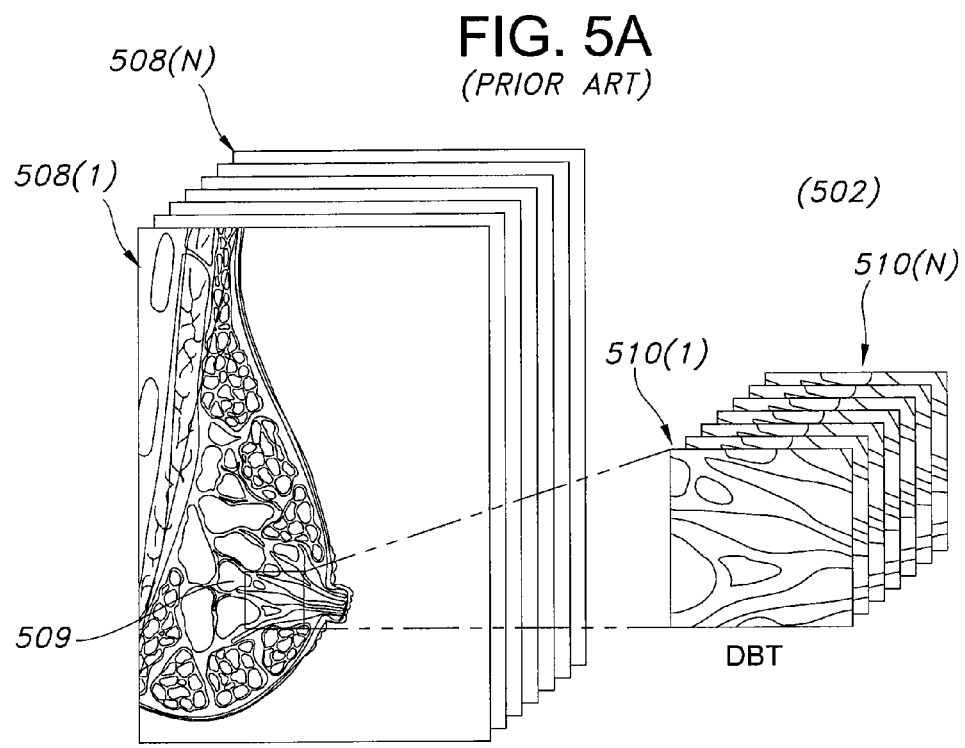
FIG. 5b is an image illustrating the selection of a ROI within a DBT image in accordance with an aspect of the present invention.

Similar to DM, the DBT system 302 depicted in FIG. 3b also compresses breast 310 between compression plate 308 and detector 312. In the DBT system, however, X-ray tube 304, which transmits x-rays 306, is rotated at different angles with respect to the compressed breast 310. As X-ray tube 304 is rotating at different angles with respect to breast 310, a 3D image represented by 508(1)-508(N) of the breast tissue is produced as shown in FIG. 5b. By combining the information from the different 2D projections, a 3D image is produced wherein the adjacent anatomical breast structures are filtered out, thus alleviating the effect of tissue superimposition. Thus, DBT imaging may offer a more accurate texture analysis of the breast tissue than DM. Suitable DM and DBT devices for use with the present invention will be understood by one of skill in the art from the description herein.

Referring back to FIG. 2, in step 204, the captured image is received. In an exemplary embodiment, the captured image is received by processor 110 (FIG. 1) from image input device 104 (FIG. 1) and stored in memory 108 (FIG. 1). For example, breast images may be received from another computer and stored in a database with memory 108. In another example, the breast images may be received directly from DM or DBT X-ray devices. In general, the images may be received from any electronic device capable of transmitting an image. Furthermore, the images may be compressed images or uncompressed images. The images may also be received over various mediums such as wired and/or wireless mediums.

Figure 4:
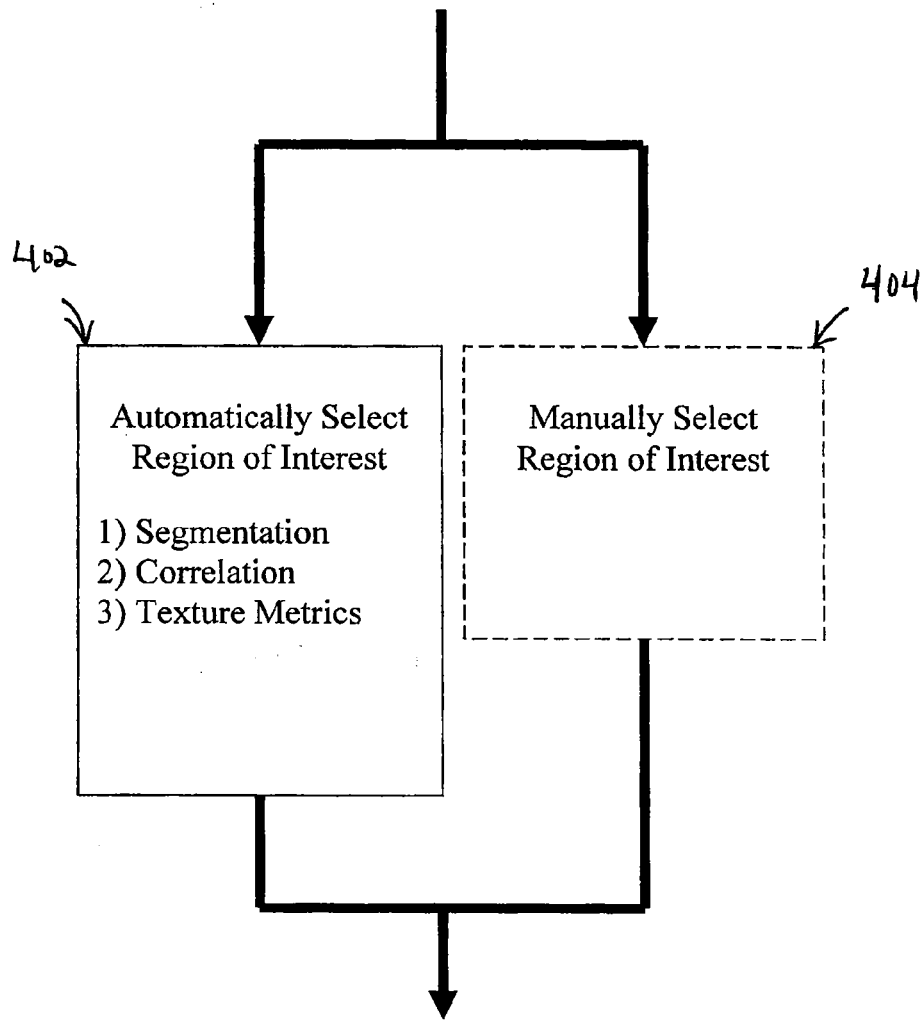
FIG. 4 is a flow diagram illustrating the selection of a ROI within am image in accordance with an aspect of the present invention.

In optional step 206, a ROI within the received image is selected. FIG. 4 depicts a flow diagram 400 of steps for selecting a ROI within a received image. Selection of the ROI is useful in assessing breast cancer risk, because the texture within the ROI is a significant contributor in the risk assessment. Analysis of an incorrect or suboptimal selected ROI may result in an erroneous assessment of breast cancer risk. It will be understood by one of skill in the art from the description herein, that the entire image may represent the ROI, in which case the selection of the ROI may be omitted because the entire image is analyzed.

Selection of the ROI within the breast image may be done either automatically (step 402) or manually (step 404) as illustrated in FIG. 4. Manually selecting the ROI within the breast image as illustrated in step 404 is generally performed by a trained professional. Specifically, measurement lines are manually drawn on the image by inputting coordinates via a computer mouse or keyboard to identify relative distances referenced to anatomic features of the breast such as the breast nipple. Manual selection of the ROI is subjective to the user who is selecting the region. Thus, different users working with the same breast image may select different regions of interest, which may lead to suboptimal selection due to human error, for example.

Automatic selection 402 of the ROI is an alternative technique which may yield more uniform selection results than manual selection 404. In one embodiment, during automatic selection of the ROI image is compared to other images in a database in order to develop anatomic correspondences. The anatomic correspondences may be established through nipple segmentation, statistical correlations such as mutual information, texture-based distance metrics, or other relevant similarity metrics. The resulting anatomic correspondences may be used to objectively map the ROI onto the images. For example, the registration correspondence may yield a coordinate transformation that is used to objectively map the canonical retroareolar ROI onto subject images. The coordinate transformation may be constrained to be topology preserving, thereby ensuring the geometric integrity of the transformed ROI used to sample the images. If necessary, multiple breast templates can be created to better reflect the distinct categories of breast anatomy that may be represented, and these templates can be determined automatically by cluster analysis of the images. The automatic selection process may also be tailored to different breast sizes and different breast morphology to better serve a wide variety of persons.

A suitable algorithm for automatic selection of a ROI may be developed using a fixed-breast population from a subset of one hundred images based on an average, representative breast size. The automated routine can be cored against the manual process to evaluate its efficacy and determine the robustness of the texture descriptors with respect to the ROI placement. The algorithm can then be optimized to operate on different breast sizes and different breast morphology for large-scale data analysis.

Figure 5C:
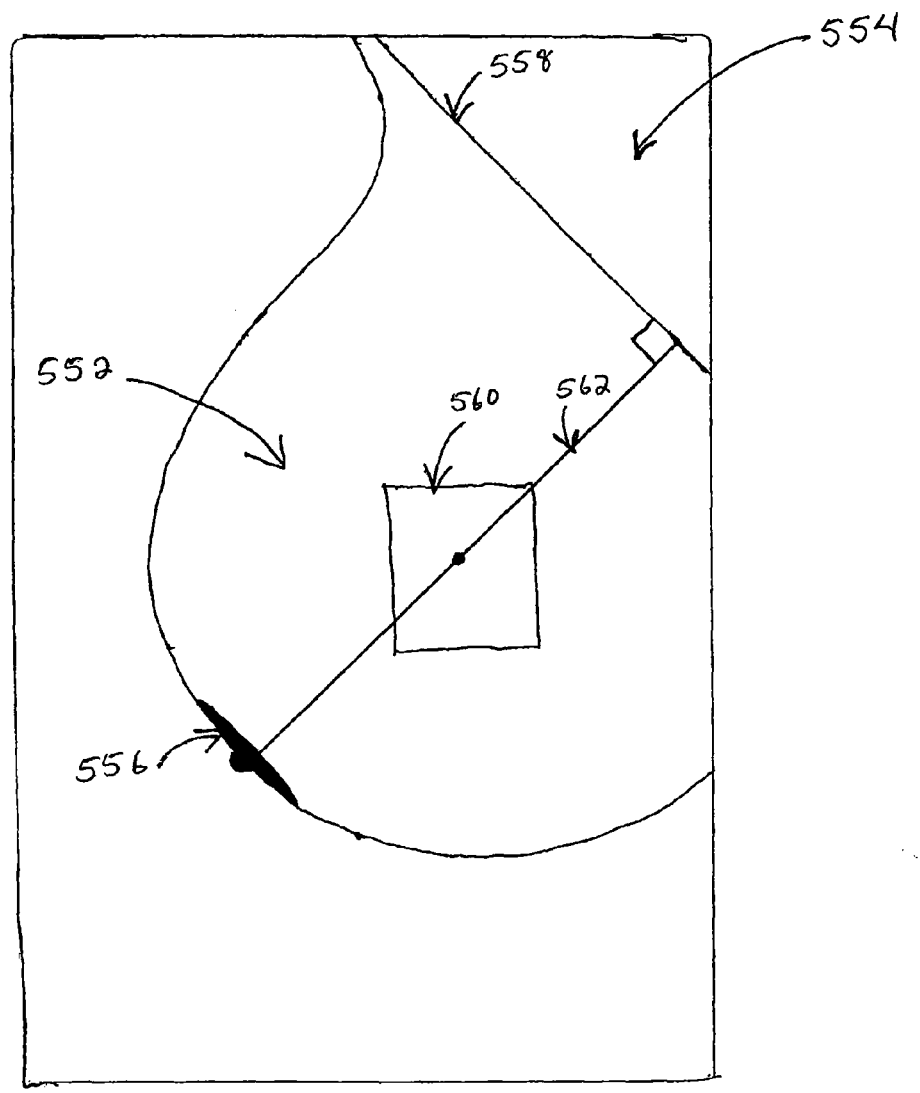
FIG. 5c is a mediolateral oblique (MLO) view image illustrating the automatic selection of a ROI within an image in accordance with an aspect of the present invention.

In one embodiment, as shown in FIG. 5c, the automatic selection of the ROI is performed for a mediolateral oblique (MLO) image of a breast 550. Once the image is loaded, the edge of the pectoral muscle is automatically located (by edge detection) and indicated by line 558. The system then automatically locates nipple 556 as being the furthest edge of breast 552 perpendicular from line 558. A perpendicular line 562 is then drawn from 558 to nipple 556. The ROI 560 is then placed in the center of line 562.

Figure 5D:
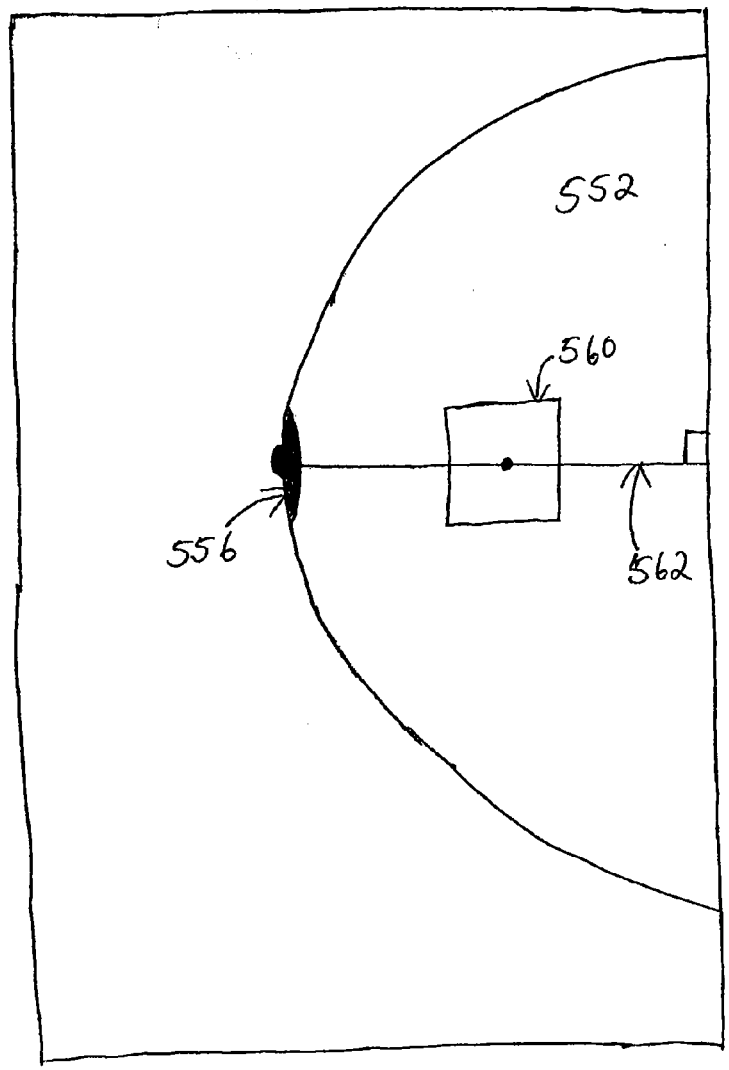
FIG. 5d is a craniocaudal (CC) view image illustrating the automatic selection of a ROI within an image in accordance with an aspect of the present invention.

In another embodiment, as shown in FIG. 5d, the automatic selection of the ROI is performed for a craniocaudal (CC) image of a breast 570. Once the image is loaded, the system automatically locates nipple 556 as being the furthest edge of breast 552 from the side of the image. A perpendicular line 562 is then drawn from the side of the image to nipple 556. The ROI 560 is then placed in the center of line 562.

In an exemplary embodiment, once the ROI is automatically placed, the ROI may then be manually adjusted by a trained professional, for example. The manual adjustment may fine tune the automatic ROI placement for obtaining a more optimal area of the breast for analysis. Furthermore, the trained professional may also manually draw pectoral line 558 in the MLO image and manually select nipple 556 in either the MLO or CC image.

FIG. 5a illustrates X-ray images 504 using a DM imaging technique 500 and FIG. 5b illustrates a 3D X-ray image represented by 508(1)-508(N) using a DBT imaging technique 502 of breasts wherein a ROI has been selected. Specifically, breast image 504, as captured by the DM imaging technique 500, illustrates a single ROI 506 represented by a square region identifier 505 mapped onto the DM image 504. In contrast, when a ROI is selected from the 3D breast image by the DBT imaging technique 502, two techniques may be employed. In accordance with a first technique, a ROI is selected within each of multiple 2D image projections that reconstruct a 3D image. In accordance with a second technique, a ROI is selected directly from a 3D image represented by (510(1)-510(N)) reconstructed from the multiple 2D image projections. In general, a region identifier 509 is either mapped onto each 2D image, thereby producing multiple 2D regions of interest, or it is mapped onto the 3D image, thereby producing one 3D ROI.

Figure 6:
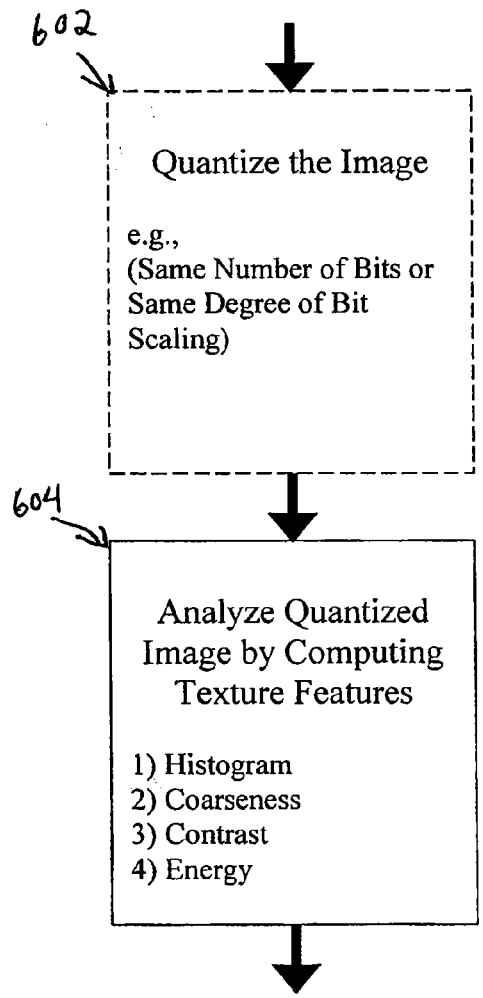
FIG. 6 is a flow diagram illustrating the analysis of an image by bit quantization and texture features in accordance with an aspect of the present invention.

Referring back to FIG. 2, in step 208 the image is analyzed, e.g., by processor 110. An embodiment for analysis of the image is now described with reference to the steps illustrated in flow diagram 600 (FIG. 6). In step 602, the pixel values within the image are quantized to a reduce bit range (step 602). Quantization may be performed using one of the two quantization algorithms described below. Other suitable algorithms will be understood by one skilled in the art from the description herein. In a first quantization algorithm, each pixel value in the ROI is quantized to the same number of bits. For example, each pixel regardless of its bit range will be quantized to one of (16, 32, 64, 128, 256, 512, 1024, 2048 . . . etc.) bits. In a second quantization algorithm, the pixels within the ROI are quantized to the same degree. Quantizing the bit ranges to the same degree may be accomplished by cutting the bit range (e.g., by ¼, ⅛, ¹⁄₁₆ . . . etc.). Quantizing the bit ranges to the same degree, may provide better accuracy for computing texture features than to the same number of bits because scaling by a certain degree does not discriminate against any particular bit range (e.g., large or small bit ranges).

In step 604, analysis of the quantized image is performed by computing one or more texture features. In general, the texture features may be computed in either 2D or 3D depending on the dimensions of the selected image. One example of a texture feature is skewness of a histogram of the image. For example, when the image is predominantly composed of fat, the histogram skewness tends to be positive, whereas when the texture is primarily composed of dense tissue, the histogram skewness tends to be negative. Skewness of a histogram is known to be the third statistical moment and may be computed in accordance with equation 1.

$$\text{skewness} = \frac{w_3}{w_2^{3/2}}, \; w_k = \sum_{i=0}^{g_{max}} n_i(i-\bar{i})^k / N, \; N = \sum_{i=0}^{g_{max}} n_i, \quad (1)$$

$$\bar{i} = \sum_{i=0}^{g_{max}} (in_i/N)$$

In equation 1, $n_i$ represents the number of times that gray level value i occurs in the image region, and $g_{max}$ is the maximum gray-level value, and N is the total number of image pixels. By computing the skewness of the ROI, the system is able to assess the density of the breast tissue.

Another example of a texture feature is coarseness. Small coarseness values indicate fine texture (high detail), whereas high coarseness value indicates coarse texture (low detail).

In one embodiment, coarseness is computed in accordance with equation 2 based on a Neighborhood Gray Tone Difference Matrix (NGTDM).

$$\text{coarseness} = \left( \sum_{i=0}^{g_{max}} p_i v(i) \right)^{-1} \text{and} \quad (2)$$

$$v(i) = \begin{cases} \sum |i - \bar{L}_i| & \text{for } i \in \{n_i\} \text{ if } n_i \neq 0 \\ 0 & \text{otherwise} \end{cases}$$

In equation 2, $g_{max}$ is the maximum gray-level value, $p_i$ is the probability that gray level i occurs, $\{n_i\}$ is the set of pixels having gray level value equal to i, and the inverse of L is calculated in accordance with equation 3 for a 2D image, or equation 4 for a 3D image.

$$\bar{L}_i = \frac{1}{S-1} \sum_{k=-t}^{t} \sum_{l=-t}^{t} j(x+k, y+l) \quad (3)$$

-continued $$\overline{L}_i = \frac{1}{S-1} \sum_{k=-t}^{t} \sum_{l=-t}^{t} \sum_{q=-t}^{t} j(x+k, y+l, z+q) \quad (4)$$

In 2D equation 3, j(x,y) is the pixel located at (x,y) with gray level value i, (k,l)≠(0,0) and $S=(2t+1)^2$ with, for example, t=1, or other suitable value, specifying the neighborhood size around the pixel located at (x,y).

In 3D equation 4, j(x,y,z) is the voxel located at (x,y,z) with gray level value i, (k,l,z)≠(0,0,0), and $S=(2t+1)^3$ with, for example, t=1, or other suitable value, specifying the 3D voxel window around (x,y,z).

Other examples of texture features are contrast and energy. Computations of contrast and energy for a 2D image are determined from a gray-level co-occurrence matrix based on the frequency of the spatial co-occurrence of gray-level intensities in the image. Computations of contrast and energy for a 3D image are determined from a gray-level co-occurrence matrix for a displacement vector within the 3D image. Specifically, the probability of occurrence of voxel pair of gray levels whose spatial locations are a selected displacement vector apart, is used to compute contrast and energy in the 3D image. In this embodiment, contrast quantifies overall variation in image intensity, while energy is a measure of image homogeneity. Contrast, energy and homogeneity may be computed in accordance with equations 5, 5 and 7 for a 2D image.

$$\text{contrast} = \sum_{i=0}^{g_{max}} \sum_{j=0}^{g_{max}} |i-j|^2 C(i,j) \quad (5)$$

$$\text{energy} = \sum_{i=0}^{g_{max}} \sum_{j=0}^{g_{max}} C(i,j) \quad (6)$$

$$\text{homogeneity} = \sum_{i=0}^{g_{max}} \sum_{j=0}^{g_{max}} \frac{C(i,j)}{1+|i-j|} \quad (7)$$

In equations 5, 6 and 7, $g_{max}$ is the maximum gray-level value and C is the normalized co-occurrence matrix.

In a 3D image, to compute contrast, energy, and homogeneity, the gray-level co-occurrence statistics required for the computation of the co-occurrence matrix are estimated based on the spatial co-occurrence frequencies of voxel gray-level values within the entire 3D ROI volume. In an exemplary embodiment, a 3D displacement vector d=(dx, dy, dz) is defined around each voxel along the x, y, and z dimensions, where dx=dy=dz=1 is the voxel offset; with 26 neighboring voxel-pairs in 13 independent symmetric directions. Texture features in this embodiment may be calculated in each of these 13 directions and then averaged to create a single measure. In alternative embodiments, more or fewer than 13 directions may be utilized. Additionally, the calculated texture features may be processed using other statistical techniques, e.g., median, mode, minimum, or maximum.

Another example of a texture feature for a 2D and 3D image, is the ratio between pixel values located in concentric circles (2D) or spheres (3D) that are centered at a central point, and pixel values of the entire ROI. The area (2D) and volume (3D) properties of the ROI obtained through this method may be utilized along with the other texture features in the logistic regression model for assessing cancer risk of a person. The volume properties of the ROI are computed utilizing equations 8 and 9.

$$f_s(i) = \frac{N_\theta(m, r_i)}{N_{SPHERE}(m, r_i)} \quad (8)$$

$$f_r(i) = \frac{N_\theta(m, r_i)}{N_\theta(m, r_k)} \quad (9)$$

In equation 8, fs measures the fraction of the circle or sphere occupied by the ROI (wherein $N_\theta(m, r_i)$ is the area or volume of the ROI intersected by the circle or sphere, and $N_{SPHERE}(m, r_i)$ is the area of the circle or the volume of the sphere). In equation 9, fr measures the fraction of the ROI occupied by the circle or sphere (wherein $N_\theta(m, r_i)$ is the area or volume of the ROI intersected by the circle or sphere, and $N_\theta(m, r_k)$ is the area of the entire ROI or the volume of the entire ROI). θ denotes a ROI constructed by a set of voxels V={$v_i$, i=1, ..., z}, wherein m is the center of mass of θ. R is a sub-region of θ that extends over a radius r from the center of mass m. For characterizing θ, we define the radial voxel counting function as:

$$N_\theta(m,r) = |\{v_i \in R\}|, \text{ where } \forall_i, v_i \in R: |m - v_i| \leq r \quad (10)$$

The radial voxel counting function $N_\theta(m, r)$ counts the number of voxels v that belong to the sub-region R. In other words, this function enumerates the voxels v that belong to the intersection of a sphere of radius r (circle for 2D ROIs) and the ROI θ.

For the non-homogeneous regions, the contribution of each voxel is determined by its density content. Hence, the alternative radial voxel density counting function for the non-homogeneous ROIs is defined as:

$$N_\theta(m, r) = \sum_i \text{density content } (v_i), \quad (11)$$

$$\text{where } \forall_i, v_i \in R : |m - v_i| \leq r$$

This alternative density counting function calculates the sum of the density content of each voxel $v_i$ that belongs to the sub-region R defined by the intersection of a sphere of radius r (circle for 2D ROIs) and the ROI θ.

Referring back to FIG. 2, in step 210, risk factors of the person are determined. Risk factors of a person require additional pieces of information that may improve the accuracy of assessing a person's breast cancer risk. In one embodiment, the risk factors that are used for breast cancer assessment are Gail risk factors. Specifically, the Gail risk factors may include unique information for each person such as, for example, current age of the person, age when the person started menstruating, previous breast biopsies of the person, age of the person at first birth, and person's family history of breast cancer in first-degree relatives. These risk factors are determined independent of analyzing the breast image.

Figure 7:
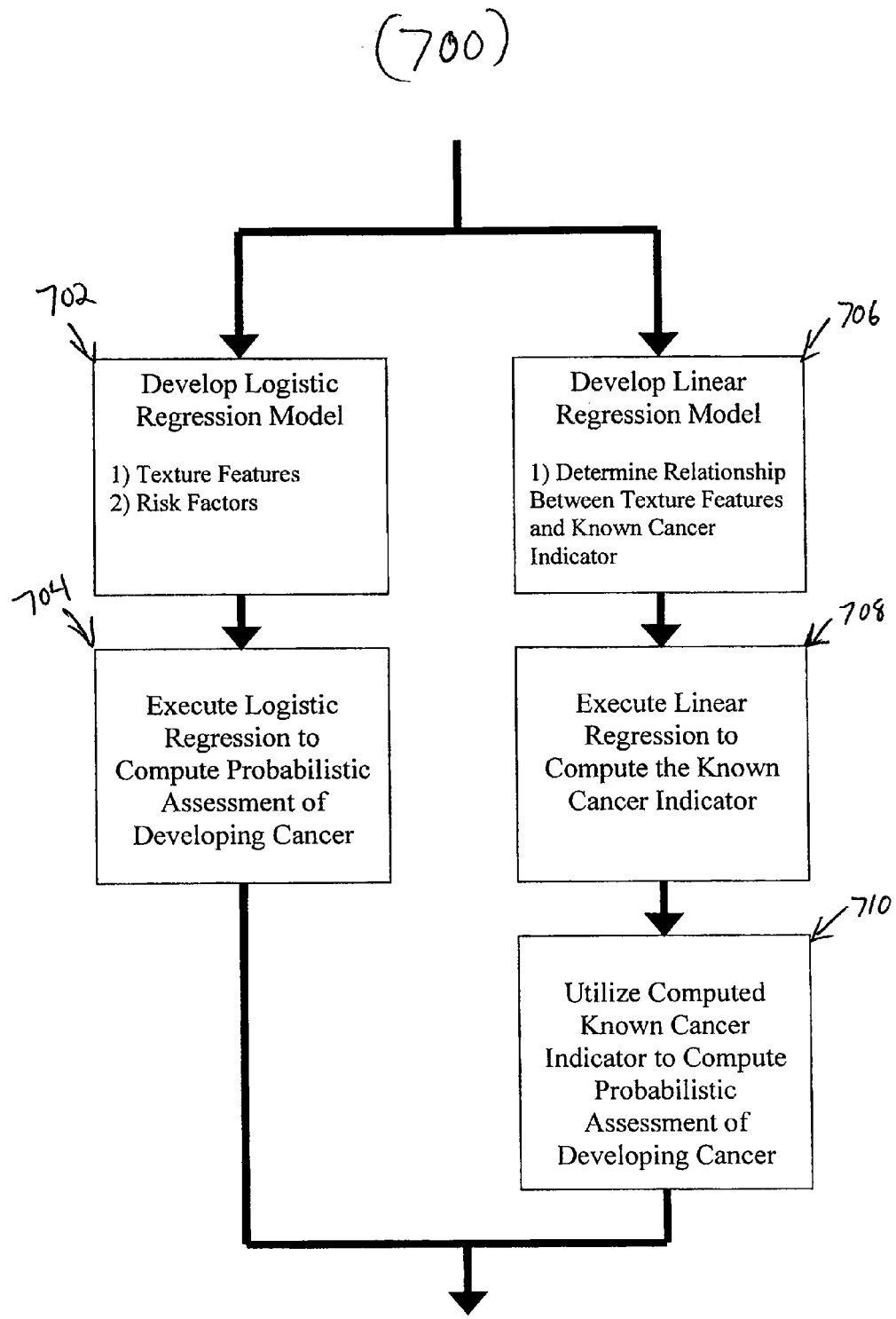
FIG. 7 is a flow diagram illustrating the development and execution of a logistic regression model based on texture features and risk factors and the development and execution of a linear regression model based on texture features and known cancer indicators for assessing cancer risk in accordance with aspects of the present invention.

In step 212, a probabilistic assessment of the person developing cancer is determined. FIG. 7 depicts a flow chart 700 of two exemplary processes for use in determining a probabilistic assessment of cancer risk. One process for assessing cancer risk is the execution of logistic regression (steps 702-704) with the texture features and risk factors. Another process to assessing cancer risk is the execution of linear regression (steps 706-710) between the texture features and a known cancer indicator such as breast density.

In step 702, a logistic regression model is developed. In one example, the model includes texture features computed by analyzing the breast image produced in step 208 (e.g., histogram skew, coarseness, energy and contrast) and person risk factors such as the Gail risk factors. The logistic regression model may be adjusted for factors such as menopause, body mass index (BMI), ethnicity, etc.

In step 704, a probabilistic assessment of developing breast cancer is developed through execution of the logistic regression model. In one example, the model expresses the log-odds (natural log of the probabilistic ratio of an event occurring versus the event not occurring) for cancer as a combination of the texture features and the potential risk factors. Determination of significant predictors may employ the log-likelihood ratio test, which is a statistical test for making a decision between two hypotheses based on the value of this ratio. The maximum likelihood estimates for the logistic regression coefficient may be obtained for each separate risk factor and the corresponding odds ratios are estimated with associated confidence intervals. The log-odds ratio provided by the model is converted into a corresponding probability of developing cancer. Thus, the system utilizes the information obtained from the texture analysis of the ROI of the breast image as well as the person-specific risk factors to perform a logistic regression thus producing a probabilistic assessment of the person developing cancer.

Breast density has been shown to correlate with a persons risk of obtaining breast cancer. Specifically, higher density correlates to higher risk of obtaining breast cancer. By performing linear regression on the extracted texture features of the image, the breast density of the person may be computed, and thus aid in the assessment of the person's cancer risk.

In step 706, a linear regression model is developed. In one example, the model includes texture features computed by analyzing the breast image produced in step 208 (e.g., histogram skewness, coarseness, energy and contrast). Linear regression shows high correlation between various texture features and breast density in both DM and DBT images. In the DBT image, as breast density increases, texture features such as coarseness, fractal dimension increase in value while features such as contrast decrease in value. Exemplary linear regression values (e.g., coefficients and statistics) of texture features versus breast density are shown in the table of FIG. 13.

Previously, breast density has been determined manually or semi-automatically based on the intensity values of the pixels within the image. This simplified determination may not be accurate because intensity values of the pixels may be high due to factors other than breast density. Additionally, manual, pixel-wise classification of an image to determine breast density, which is typically performed using gray-level image thresholding, is subjective with high inter-observer variability. Also, these techniques are not fully automated and are difficult to standardize. With the strong correlations between the texture features and a known breast density, however, a more accurate determination of breast density may be attained. By increasing the accuracy in computing breast density in step 708, the accuracy of the breast cancer risk assessment in step 710 is also increased.

In this embodiment, breast density is utilized as the known cancer indicator correlated with the texture features. It is contemplated that other known indicators could also be used in assessing breast cancer risk. It is also contemplated that when dealing with other types of cancer (e.g. brain, lung, oral etc.) that other known indicators which are correlated with the texture features may be used to assess cancer risk.

Image quality is important in making an accurate assessment of cancer risk. In general, assessments made from images with high quality scores may be trusted more, whereas assessments made from images with low image quality scores may be trusted less. The relationship between image acquisition parameters of an imaging device and texture features estimate signal to noise ratio, which may be utilized to compute an image quality score. By performing linear regression, the relationship between the image acquisition parameters of the imager and texture features of the image may be modeled in order to access the image quality score.

In various embodiments of the invention, cancer risk of a patient is assessed based on texture features within the image. The accuracy of these texture features may deteriorate due to poor image quality thereby reducing the reliability of the assessment. In general, image quality is dependent on noise contributed by the patient and the system. For example, system noise in an image may be due to sub-acquisition parameters on the X-ray machine or deterioration of the X-ray machine. Patient noise in an image may be due to anatomical features such as skin and fat tissue, or may be due to sub-optimal positioning of the patient during the X-ray. Additionally, image quality may be affected by the technician improperly performing the test, e.g., by setting up the equipment incorrectly or improperly positioning the patient on the equipment during the test.

To improve the reliability of the cancer risk assessment, it may be beneficial to determine the quality of the image. In step 218 of FIG. 2, an evaluation is performed to determine the quality of the image. Step 218 is shown in greater detail in FIG. 8 as steps 802 and 804. Alternatively, the quality of the image may be determined independently from assessing cancer risk. For example, the quality of the image may be used to determine if the imaging equipment needs to be repaired/replaced, or to support the diagnostic decision of the interpreting radiologist.

Figure 8:
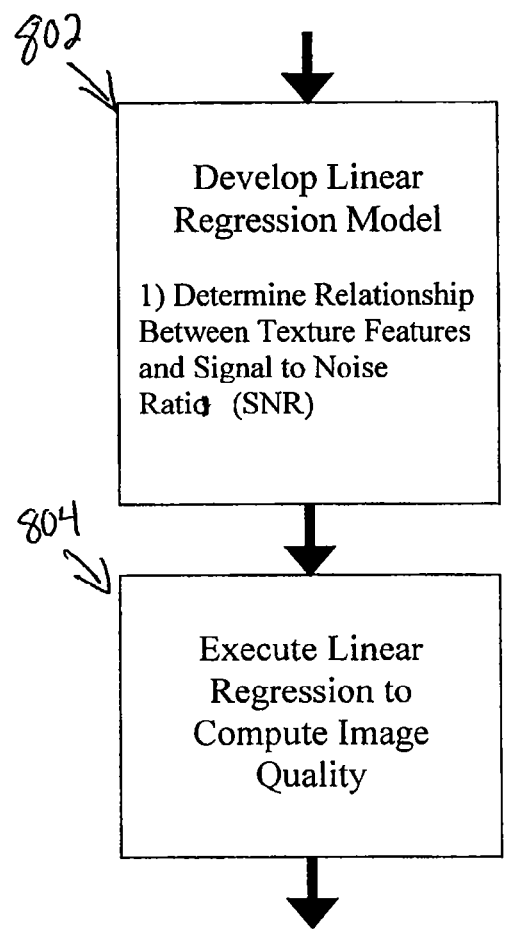
FIG. 8 is a flow diagram illustrating the development and execution of a linear regression model to estimate signal to noise ratio (SNR) based on texture features for assessing image quality in accordance with an aspect of the present invention.

FIG. 8 depicts a flow diagram illustrating the development and execution of a linear regression model to estimate signal to noise ratio (SNR) based on texture features for assessing image quality in accordance with an aspect of the present invention. At step 802, a linear regression model is developed. The linear regression model may be developed by determining the relationship between texture features and signal to noise ratio (SNR). At step 804, a linear regression is executed to compute image quality.

In FIGS. 9 and 10, linear regression is shown to have a strong correlation between various texture features/acquisition parameters and signal to noise ratio (SNR) of the image and, in FIGS. 11 and 12, linear regression is shown to have a strong correlation between various texture features/acquisition parameters and dose of the image.

As SNR increases, texture features such as skewness, coarseness and fractal dimension increase in value while features such as contrast, energy and homogeneity decrease in value. Likewise, as dose increases, texture features such as skewness, coarseness and fractal dimension increase in value while features such as contrast, energy and homogeneity decrease in value. Exemplary stepwise multiple linear regression values of texture features versus SNR are shown in the table of FIG. 9 and versus dose are shown in the table of FIG. 11.

In another embodiment, when utilizing acquisition parameters such as target/filter and kilo-volt (kV) as additional predictor variables in the linear regression, a stronger correlation to SNR is observed. Also, when utilizing acquisition parameters such as target/filter and kilo-volt (kV) as additional predictor variables in the linear regression, a stronger correlation to dose is observed. Exemplary stepwise multiple linear regression values of texture features and acquisition parameters versus SNR are shown in the table of FIG. 10 and versus dose are shown in the table of FIG. 12.

With the strong correlations shown in FIGS. 9, 10, 11, and 12, the quality of the image may therefore be accurately computed by the texture features and/or acquisition parameters. In one example, once the image quality is determined, a hard pass/fail decision may be output from the image quality assessment step 218 to the cancer risk assessment step 212 in FIG. 2. If the hard decision indicates a failure (computed SNR is low), the probabilistic assessment for that image may be discarded. After the failure, a new image may be taken and the test may be performed again. If the image fails multiple times, the X-ray machine may be taken offline (i.e. removed from service) for maintenance.

In another example, if a soft decision is output from the image quality assessment step 218 to the cancer assessment step 212, the probabilistic assessment of cancer may be tagged with a soft reliability number between 0% (minimum reliability) and 100% (maximum reliability). For example, if the soft decision indicates a poor SNR value, the probabilistic assessment of cancer may be tagged with a poor reliability number such as 30%. The trained professional may then vary the acquisition parameters and obtain a new image to re-test the patient in an attempt to increase the reliability number to an adequate SNR threshold. Providing feedback of the reliability number allows the trained professional to determine the effects of varying acquisition parameters on the image quality. There is a strong correlation between textures of a woman's left and right breast. This strong correlation indicates that certain texture features are inherent in a particular person. Thus, the extracted texture features of the image may be used to determine a unique identifier for each person (e.g. similar to a fingerprint). By performing linear regression on the extracted texture features of the image, a unique identifier for each person may be established. A possible use for the established unique identifier may be for identifying one person from another. Correctly identifying a persons image is critical for minimizing insurance fraud (the same image cannot be claimed by multiple persons), as well as malpractice (the image cannot be mistaken for the wrong person).

In step 214 the assessment is stored in memory and in step 216 the assessment is displayed. In one example, the assessment may be stored by processor 110 (FIG. 1) in memory 108 for permanent storage. In another example, the assessment may be temporarily stored in memory 108 (which acts as a buffer) prior to display by display 106.

The various aspects of the present invention discussed above, provide the following advantages:

One advantage is a fully automated system for accurately accessing cancer risk of a person. The fully automated system removes the burden of estimating risk from the technician/practitioner, and also minimizes human error. The automated assessment is useful in tailoring cancer treatments and forming preventive strategies, especially for women at high risk. Thus, a more comprehensive and personalized assessment can be provided utilizing techniques of the present invention.

Another advantage is the personal assessment of each person dependent on an automatically generated logistic regression model. The logistic regression model provides an assessment that is tailored to each persons unique features, thus more accurately assessing cancer on a personal level.

Another advantage is the personal assessment of each person dependent on an automatically generated linear regression model. The linear regression model computes a known risk factor such as breast density to assess cancer.

Another advantage is determining a unique identifier for each person. The unique identifier ensures correct identification of each image, thus preventing insurance fraud (same image cannot be used under different names), identity theft (unique identifier is not usable like a social security number) and malpractice (images cannot be mixed up).

Another advantage is determining image quality. Image quality affects texture features of an image, and thus cancer assessment. Determining image quality allows the system to perform a more accurate assessment of cancer risk.

One or more of the steps described above may be embodied in computer program instructions for execution by a computer. The computer program instructions, when executed by a computer, cause the computer to perform these one or more steps. The computer program instructions may be embodied in computer readable media.

Although the invention illustrated and described herein with specific embodiments, the invention is not intended to be limited to the details shown, rather various modifications may be made and the details within the scope and range equivalents of the claims and without departing from the invention. For example, although the present invention has been described for use in determining the risk of developing breast cancer, it is it is contemplated that the method can be used to assess the risk of developing other types of cancer, e.g., brain, lung, oral, etc.

What is claimed:

1. A method for assessing risk of developing cancer, comprising:
    receiving an image of a person;
    analyzing the image to determine texture values representing characteristics of the image;
    calculating a unique identifier for the person using the determined texture values, the texture values for calculating the unique identifier including skewness, coarseness, and contrast;
    obtaining risk factors associated with the person;
    determining a probabilistic assessment of the person developing cancer based on the determined texture values and the obtained risk factors; and
    storing the probabilistic assessment.

2. The method of claim 1, wherein the received image is a breast image.

3. The method of claim 2, wherein the breast image is a digital mammography (DM) image.

4. The method of claim 2, wherein the breast image is a digital breast tomosynthesis (DBT) image.

5. The method of claim 1, wherein the analyzing step includes:
    selecting a region of interest within the image; and
    analyzing the image within the selected region of interest to obtain the values representing characteristics of the image.

6. The method of claim 5, wherein the selecting step comprises:
    manually selecting the region of interest within the image.

7. The method of claim 5, wherein the selecting step comprises:
    automatically selecting the region of interest within the image by comparing the image to other images to establish anatomic correspondences, the anatomic correspondences established by segmentation, statistical correlations and texture metrics.

8. The method of claim 7, wherein the image is a mediolateral oblique (MLO) view of a breast image and the automatically selecting includes:
    locating a pectoral muscle;
    locating a nipple;
    drawing a line perpendicular from the pectoral muscle to the nipple; and selecting the region of interest at a point along the perpendicular line.

9. The method of claim 7, wherein the image is a craniocaudal (CC) view of a breast image and the automatically selecting includes:
locating a side of the image;
locating a nipple;
drawing a line perpendicular from the side of the image to the nipple; and
selecting the region of interest at a point along the perpendicular line.

10. The method of claim 5, wherein the determined texture values representing the characteristics of the image further include energy of the region of interest (ROI), ratios between the pixel values in the ROI and pixel values in a segmented portion of the ROI.

11. The method of claim 5, wherein a computer is programmed to determine the probabilistic assessment by developing a logistic regression model based on at least one image feature of the region of interest and the risk factors associated with the person and determining the probabilistic estimation of the person developing cancer based on the logistic regression model.

12. The method of claim 11, wherein the at least one image feature is a texture value.

13. The method of claim 5, wherein the selecting step comprises:
comparing the image with other images to establish anatomic correspondences; and
mapping a region identifier onto the image to select the region of interest based on the anatomic correspondences.

14. The method of claim 5, wherein a computer is programmed to determine the probabilistic assessment by developing a linear regression model based on at least one image feature of the selected region of interest and breast density and determining the probabilistic estimation of the person developing cancer based on the linear regression model.

15. The method of claim 14, wherein the at least one image feature is a texture value.

16. The method of claim 1, further comprising:
developing a linear regression model based on texture features of the region of interest and signal to noise ratio (SNR) of the image; and
determining image quality based on the linear regression model.

17. The method of claim 1, wherein a computer is programmed to determine the probabilistic assessment of the person developing cancer.

18. A method for developing a logistic regression model for a person developing breast cancer, comprising:
receiving an image of breast tissue for a person;
selecting a region of interest within the image;
analyzing the region of interest to determine texture values of the image;
calculating a unique identifier for the person using the determined texture values, wherein the texture values for calculating the unique identifier include skewness, coarseness, and contrast;
developing a logistic regression model, by a computer programmed to develop the logistic regression model based on the texture values in the region of interest and risk factors associated with the person for use in determining a probabilistic assessment; and
storing the logistic regression model.

19. The method of claim 18, wherein the logistic regression model is developed utilizing the risk factors, the risk factors computed from person information.

20. The method of claim 19, wherein the risk factors include Gail factors.

21. The method of claim 20, wherein the Gail factors comprise one or more of: current age of the person, age when the person started menstruating, previous breast biopsies of the person, age of person at first birth, and persons family history of breast cancer in first-degree relatives.

22. The method of claim 18, wherein the texture values further include at least one of ratios between the pixel values in the region of interest (ROI) and pixel values in a segmented portion of the ROI or energy.

23. A system for assessing risk of developing cancer, comprising:
means for receiving an image of a person;
means for analyzing the image to determine texture values representing characteristics of the image;
means for calculating a unique identifier for the person using the determined texture values, the texture values for calculating the unique identifier including skewness, coarseness, and contrast;
means for obtaining risk factors associated with the person;
means for determining a probabilistic assessment of the person developing cancer based on the determined texture values and the obtained risk factors; and
means for storing the probabilistic assessment.

* * * * *